United States Patent
Ananthapadmanabhan et al.

(10) Patent No.: US 8,732,887 B2
(45) Date of Patent: May 27, 2014

(54) PERSONAL CARE IMPLEMENT WITH LOW ACTIVE CLEANSING COMPOSITION

(75) Inventors: Kavssery Parameswaran Ananthapadmanabhan, Woodbury, CT (US); Bivash Ranjan Dasgupta, Hamden, CT (US); Prabhjyot Singh, Stratford, CT (US); Chandra Sekhar Palla-Venkata, Hamden, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 549 days.

(21) Appl. No.: 12/962,752

(22) Filed: Dec. 8, 2010

(65) Prior Publication Data

US 2012/0145171 A1    Jun. 14, 2012

(51) Int. Cl.
*A47L 23/04*   (2006.01)
*C11D 17/00*   (2006.01)

(52) U.S. Cl.
USPC .............................. 15/118; 510/438; 510/439

(58) Field of Classification Search
USPC .................................... 510/438, 439; 15/118
IPC .................................. C11D 17/00; A47L 23/04
See application file for complete search history.

(56) References Cited

U.S. PATENT DOCUMENTS

| | | | | | |
|---|---|---|---|---|---|
| 2,817,865 | A | * | 12/1957 | Arioli | 401/201 |
| 2,958,885 | A | * | 11/1960 | Donney | 401/196 |
| 3,226,751 | A | * | 1/1966 | Lemelson | 15/118 |
| 3,414,928 | A | * | 12/1968 | Lemelson | 15/118 |
| 4,190,550 | A | * | 2/1980 | Campbell | 15/104.93 |
| 4,343,061 | A | * | 8/1982 | Hanazono | 15/244.3 |
| 4,462,135 | A | | 7/1984 | Sanford | |
| 4,674,237 | A | * | 6/1987 | Sullivan | 451/523 |
| 4,821,360 | A | * | 4/1989 | Giallourakis | 15/244.3 |
| 5,295,280 | A | | 3/1994 | Hudson et al. | |
| 5,298,280 | A | * | 3/1994 | Kaczur et al. | 427/125 |
| 5,462,378 | A | * | 10/1995 | Webb | 401/201 |
| 5,626,512 | A | * | 5/1997 | Palaikis et al. | 451/536 |
| 5,640,737 | A | * | 6/1997 | Boggs | 15/118 |
| 5,650,384 | A | | 7/1997 | Gordon et al. | |
| 5,804,539 | A | | 9/1998 | Gordon et al. | |
| 5,813,523 | A | * | 9/1998 | Gnadt et al. | 206/77.1 |
| 5,839,842 | A | * | 11/1998 | Wanat et al. | 401/201 |
| 5,916,586 | A | * | 6/1999 | Villa et al. | 424/443 |
| 5,951,991 | A | * | 9/1999 | Wagner et al. | 424/401 |
| 5,955,417 | A | * | 9/1999 | Taylor | 510/438 |

(Continued)

FOREIGN PATENT DOCUMENTS

| WO | WO 9707780 A1 | * | 3/1997 | A61K 7/50 |
|---|---|---|---|---|
| WO | WO 0154661 A1 | | 8/2001 | |

OTHER PUBLICATIONS

PCT international Search Report in PCT application PCT/EP2011/070020, mailed Feb. 21, 2012.

(Continued)

*Primary Examiner* — Lee D Wilson
*Assistant Examiner* — Marc Carlson
(74) *Attorney, Agent, or Firm* — Alan A. Bornstein (57) ABSTRACT

A personal care implement is disclosed having a water insoluble absorbent/adsorbent layer attached to a water insoluble scrubbing layer and a mild, low active, low viscosity cleansing composition contained in the absorbent/adsorbent layer. A sufficient quantity of the composition is transferred on demand to the scrubbing layer by squeezing the implement. The implement produces copious quantities of lather foam and mild cleansing.

12 Claims, 4 Drawing Sheets

(56) References Cited

U.S. PATENT DOCUMENTS

| | | | |
|---|---|---|---|
| 5,977,039 A * | 11/1999 | Gordon et al. | 510/130 |
| 5,983,435 A | 11/1999 | Osborne | |
| 5,990,181 A * | 11/1999 | Spyropoulos et al. | 516/118 |
| 6,015,242 A * | 1/2000 | Gillis | 401/201 |
| 6,020,422 A * | 2/2000 | Connors et al. | 524/716 |
| 6,042,288 A * | 3/2000 | Rattinger et al. | 401/201 |
| 6,066,607 A * | 5/2000 | Gordon et al. | 510/130 |
| 6,085,380 A * | 7/2000 | Gonda et al. | 15/207.2 |
| 6,132,746 A * | 10/2000 | Hasenoehrl et al. | 424/402 |
| 6,267,975 B1 * | 7/2001 | Smith et al. | 424/401 |
| 6,322,801 B1 * | 11/2001 | Lorenzi et al. | 424/402 |
| 6,326,339 B1 * | 12/2001 | Rattinger et al. | 510/140 |
| 6,413,000 B1 | 7/2002 | Borcherds et al. | |
| 6,547,063 B1 * | 4/2003 | Zaveri et al. | 206/219 |
| 6,852,681 B1 * | 2/2005 | Kerschner et al. | 510/152 |
| 6,893,182 B1 | 5/2005 | Liao | |
| 6,957,924 B1 * | 10/2005 | McMeekin et al. | 401/201 |
| 7,115,551 B2 * | 10/2006 | Hasenoehrl et al. | 510/438 |
| 7,179,772 B2 * | 2/2007 | Keenan et al. | 510/130 |
| 7,232,364 B2 * | 6/2007 | Hibbard | 451/526 |
| 7,232,794 B2 * | 6/2007 | Huyhn et al. | 510/438 |
| 7,348,299 B2 * | 3/2008 | Keenan et al. | 510/141 |
| 7,470,656 B2 * | 12/2008 | Sherry et al. | 510/438 |
| 7,846,462 B2 * | 12/2010 | Spadini et al. | 424/402 |
| 2003/0014824 A1 | 1/2003 | Farmer | |
| 2003/0086962 A1 * | 5/2003 | Westerfield et al. | 424/443 |
| 2003/0127108 A1 * | 7/2003 | Policicchio et al. | 134/6 |
| 2004/0176002 A1 | 9/2004 | Siegwart | |
| 2004/0185730 A1 | 9/2004 | Lambino et al. | |
| 2004/0226123 A1 * | 11/2004 | Policicchio et al. | 15/115 |
| 2006/0079416 A1 | 4/2006 | Myers | |
| 2007/0039116 A1 | 2/2007 | Woodard et al. | |
| 2007/0071537 A1 * | 3/2007 | Reddy et al. | 401/196 |
| 2007/0269259 A9 * | 11/2007 | Shaw | 401/201 |
| 2008/0247806 A1 | 10/2008 | Todd et al. | |
| 2009/0155373 A1 * | 6/2009 | Huang et al. | 424/499 |
| 2009/0312223 A1 * | 12/2009 | Yang et al. | 510/407 |
| 2011/0195098 A1 * | 8/2011 | Glenn et al. | 424/401 |
| 2011/0245124 A1 * | 10/2011 | Tsaur et al. | 510/127 |
| 2011/0245125 A1 * | 10/2011 | Tsaur et al. | 510/127 |
| 2011/0245126 A1 * | 10/2011 | Tsaur et al. | 510/159 |
| 2012/0102668 A1 * | 5/2012 | De Leersnyder et al. | 15/104.93 |
| 2012/0145171 A1 | 6/2012 | Ananthapadmanabhan et al. | 132/200 |
| 2012/0246851 A1 * | 10/2012 | Smith et al. | 15/104.93 |

OTHER PUBLICATIONS

PCT international Written Opinion in PCT Application PCT/EP2011/070020.

\* cited by examiner

PERSONAL CARE IMPLEMENT WITH LOW ACTIVE CLEANSING COMPOSITION

BACKGROUND

1. Field of the Invention

The invention relates to a personal cleansing implement that is used with a low active liquid cleanser.

2. Description of the Related Art

Personal cleansing products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use. Low active cleansing products have been found generally to provide less irritation or damage to the skin or hair but suffer from poor sensory properties and therefore find less use than conventional high active cleansers. Conventional cleansing products have also been combined with various cleansing implements composed of water insoluble substrates to improve convenience to the user.

Washing implement and conventional cleanser combinations are known. For example U.S. Pat. No. 5,650,384 (Gordon et al.) issued on Jul. 22, 1997; U.S. Pat. No. 5,916,586 (Villa et al.) issued on Jun. 29, 1999; U.S. Pat. No. 6,413,000 (Borcherds et al.) issued Jul. 2, 2002; and U.S. Pat. No. 5,813,523 (Gnadt et al.) issued on Sep. 29, 1998 all disclose systems for cleansing the skin comprising a hydrophobic diamond-mesh sponge and conventional liquid cleansing and moisturizing compositions with excellent lather in the same washing and rinsing operation. The systems are reported to provide improved lather and overall acceptability for liquid cleansing compositions which may contain moisturizers.

Washing implements that combine water insoluble absorbent substrates and water insoluble scrubbing substrates are known. For example U.S. Pat. No. 3,226,751 (Lemelson) issued on Jan. 4, 1966; U.S. Pat. No. 3,414,928 (Lemelson) issued on Oct. 22, 1965; U.S. Patent Publication No. 2007/0039116 (Woodard et al.) published on Feb. 22, 2007; and U.S. Patent Publication No. 2004/0176002 (Siegart) published on Sep. 9, 2004 all disclose such combination implements some of which may be pre-impregnated with a cleansing composition.

Surprisingly, it has been found that a combination cleansing implement that includes specifically defined water insoluble substrates may be used with a low active cleansing composition not generally used for bathing to achieve the benefits of mild cleansing along with excellent sensory properties of copious lather production.

SUMMARY OF THE INVENTION

In one aspect of the invention is a cleansing product, including but not limited to:

a. an implement including a first layer attached to a second layer, wherein the first layer is composed of water insoluble scrubbing substrate and the second layer is composed of a water insoluble absorbent/adsorbent substrate;

b. a low active liquid cleansing composition containing about 0.1 to 8% by wt. of total lathering surfactant(s);

c. wherein the cleansing composition is contained in the second layer; and d. wherein the second layer can retain at least 5 grams of the liquid cleansing composition (defined as being able to hold a specified quantity of the composition without noticeable leakage in 15 seconds) and wherein the second layer has a Compressibility Factor of at least 5% (defined as the % of the liquid cleansing composition contained by the second layer that is transferred to the first layer by a user squeezing the implement using a pressure in the range of about 3 to 12 psi).

In another aspect of the invention is a cleansing product kit, including but not limited to:

a. a substantially dry implement including a first layer attached to a second layer, wherein the first layer is composed of scrubbing substrate and the second layer is composed of an absorbent/adsorbent substrate; (substantially dry is herein defined as the implement containing less than 5, 4, 3, 2, 1, or 0.5% by wt. of water based on the dry weight of the implement)

b. a liquid cleansing composition supplied in a container in combination with the implement containing about 0.1 to 8% by wt. of total lathering surfactant(s);

c. wherein the second layer can contain at least 5 grams for the composition and has a Compressibility Factor of at least 5%; and d. optionally instructions for use of the cleansing product kit.

In a further aspect of the invention is a method of cleansing the skin or hair, including but not limited to the steps of:

a. providing a cleansing implement including a first layer attached to a second layer, wherein the first layer is composed of scrubbing substrate and the second layer is composed of an absorbent/adsorbent substrate;

b. wherein the second layer is supplied with at least 5 grams of a cleansing composition containing about 0.1 to 8% by wt. of total lathering surfactant(s) prior to cleansing the skin or hair; and c. adding water to the implement while manually compressing and releasing the implement to transfer a sufficient quantity of cleansing composition to the scrubbing substrate to generate lather.

DETAILED DESCRIPTION OF THE INVENTION

Figure 1:
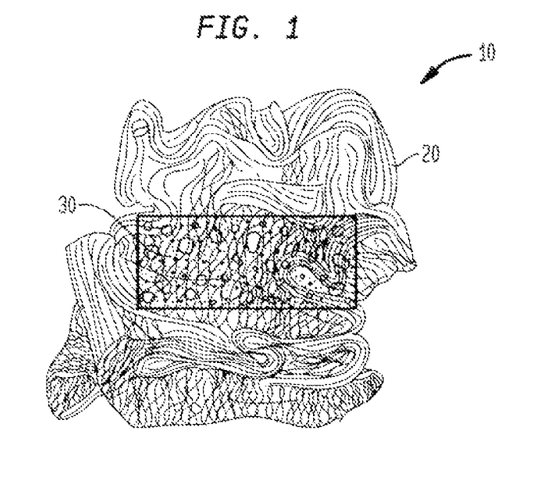
FIG. 1 is a front elevational view of a cleansing implement representing an embodiment of this invention containing scrubbing and sponge substrates.
Figure 2:
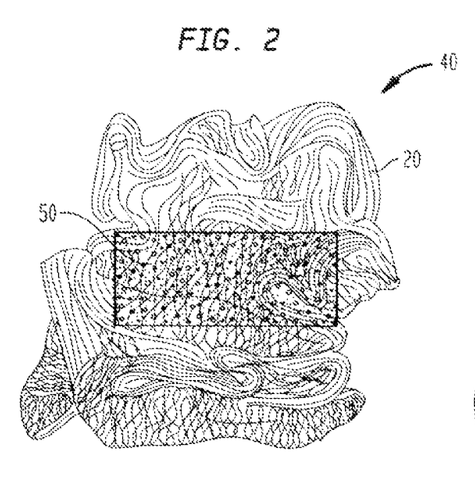
FIG. 2 is a front elevational view of a cleansing implement representing an embodiment of this invention containing scrubbing and nonwoven substrates.
Figure 3:
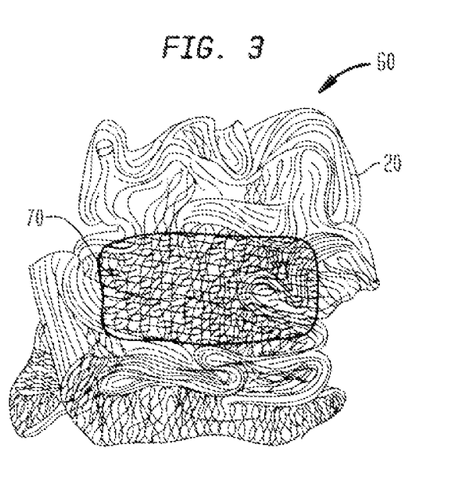
FIG. 3 is a front elevational view of a cleansing implement representing an embodiment of this invention containing scrubbing and woven substrates.

Referring now to the drawings in which like figures represent like elements, FIGS. 1 to 3 depict cleansing implements where the water insoluble absorbent/adsorbent substrate is secured to and at least partially surrounded by the water insoluble scrubbing substrate. More specifically, in FIG. 1, cleansing implement 10 is made up of a water insoluble scrubbing substrate 20 and water insoluble absorbent/adsorbent sponge substrate 30 substrate partially surrounded by scrubbing substrate 20. In another embodiment of the invention FIG. 2 illustrates cleansing implement 40 that is made up of a water insoluble scrubbing substrate 20 and water insoluble absorbent/adsorbent nonwoven substrate 50 substrate partially surrounded by scrubbing substrate 20. Similarly in FIG. 3, cleansing implement 60 is made up of a water insoluble scrubbing substrate 20 and water insoluble absorbent/adsorbent woven substrate 70 substrate partially surrounded by scrubbing substrate 20. In another preferred embodiment (not illustrated) the absorbent/adsorbent substrate is completely surrounded by the scrubbing substrate.

Figure 4:
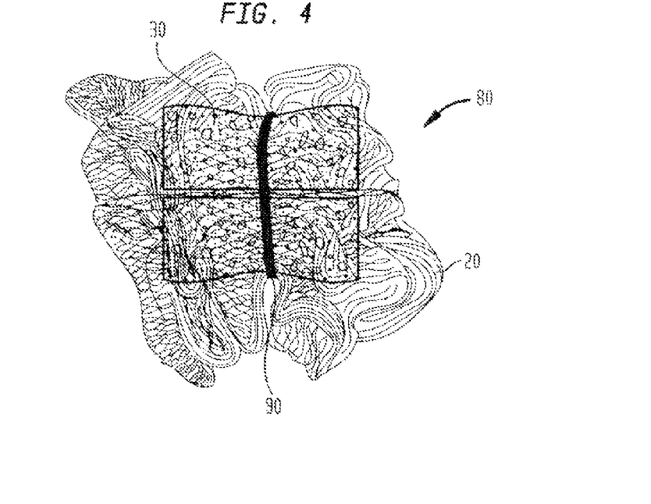
FIG. 4 is a front elevational view of a cleansing implement representing an embodiment of this invention containing scrubbing and sponge substrates.
Figure 5:
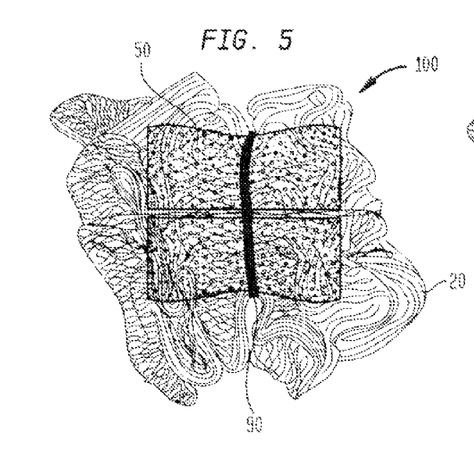
FIG. 5 is a front elevational view of a cleansing implement representing an embodiment of this invention containing scrubbing and nonwoven substrates.
Figure 6:
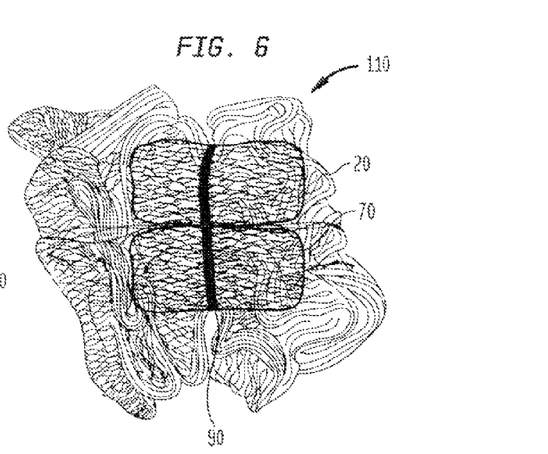
FIG. 6 is a front elevational view of a cleansing implement representing an embodiment of this invention containing scrubbing and woven substrates.

FIGS. 4 to 6 depict cleansing implements where the water insoluble absorbent/adsorbent substrate is secured to the water insoluble scrubbing substrate in a side by side arrangement. More specifically, in FIG. 4, cleansing implement 80 is made up of a water insoluble scrubbing substrate 20 and water insoluble absorbent/adsorbent sponge substrate 30 substrate secured to scrubbing substrate 20 by cord 90. In another embodiment of the invention FIG. 5 illustrates cleansing implement 100 that is made up of a water insoluble scrubbing substrate 20 and water insoluble absorbent/adsorbent nonwoven substrate 50 substrate secured to scrubbing substrate 20 by cord 90. Similarly in FIG. 6, cleansing implement 110 is made up of a water insoluble scrubbing substrate 20 and water insoluble absorbent/adsorbent woven substrate 70 substrate secured to scrubbing substrate 20 by cord 90.

In one aspect of the invention is a cleansing product, including but not limited to:

a. an implement including a first layer attached to a second layer, wherein the first layer is composed of water insoluble scrubbing substrate and the second layer is composed of a water insoluble absorbent/adsorbent substrate;

b. a low active liquid cleansing composition containing about 0.1 to 8% by wt. of total lathering surfactant(s);

c. wherein the cleansing composition is contained in the second layer; and d. wherein the second layer can retain at least 5 grams of the liquid cleansing composition and wherein the second layer has a Compressibility Factor of at least 5%. Preferably the upper limit to the compressibility factor is 50%.

Preferably the scrubbing substrate is composed of polymeric mesh sponge having a plurality of plies of an extruded tubular netting mesh and the second layer is composed of material selected from sponge material, fibrous material or a combination thereof. More preferably the length of the implement along its major axis is less than 15 cm. Most preferably the implement is dimensioned to fit substantially within the user's hand.

Advantageously the liquid cleansing composition has a dilution profile whereby the viscosity is lowered to 0.1 Pa·s or less measured at a water dilution factor of 1.5 or 2.0 and a shear rate of 10 s−1 at 35° C. In other preferred embodiments the liquid cleansing composition includes water soluble or dispersible thickener(s) in the total concentration range of 0 to about 10% by wt. and hydrophilic conditioning agent(s) in a total concentration range of 0 to about 10% by wt. Preferably the thickener is selected from water soluble or dispersible natural or synthetic polymer(s) or blends thereof.

Preferably the lather foam volume produced by the implement and cleansing composition as measured by the standard Lather Foam Measurement test is greater than 700, 800, 900 or 1000 mls. Advantageously the implement may have the scrubbing layer arranged substantially around the absorbent/adsorbent layer or have the scrubbing layer and absorbent/adsorbent layer positioned in a substantially side by side arrangement. More preferably the absorbent/adsorbent layer has the capacity to contain about 5 to 40 gms of the liquid cleansing composition.

In a preferred embodiment the cleansing composition includes lathering surfactants selected from soap, synthetic anionic surfactant(s), cationic surfactant(s), amphoteric surfactant(s), nonionic surfactants or blends thereof.

In another aspect of the invention is a cleansing product kit, including but not limited to:

a. a substantially dry implement including a first layer attached to a second layer, wherein the first layer is composed of scrubbing substrate and the second layer is composed of an absorbent/adsorbent substrate;

b. a liquid cleansing composition supplied in a container in combination with the implement containing about 0.1 to 8% by wt. of total lathering surfactant(s);

c. wherein the second layer can contain at least 5 grams for the composition and has a Compressibility Factor of at least 5%; and d. optionally instructions for use of the cleansing product kit.

In a further aspect of the invention is a method of cleansing the skin or hair, including but not limited to the steps of:

a. providing a cleansing implement including a first layer attached to a second layer, wherein the first layer is composed of scrubbing substrate and the second layer is composed of an absorbent/adsorbent substrate;

b. wherein the second layer is supplied with at least 5 grams of a cleansing composition containing about 0.1 to 8% by wt. of total lathering surfactant(s) prior to cleansing the skin or hair; and c. adding water to the implement while manually compressing and releasing the implement to transfer a sufficient quantity of cleansing composition to the scrubbing substrate to generate lather.

The inventive personal care implement contains at least two water insoluble substrates composed of a scrubbing substrate attached to a absorbent/adsorbent substrate. The substrates may be attached using one or a combination of weaving, sewing, stapling, adhesive or heat activated bonding, tying, or otherwise being integrated together by any art recognized technique in a manner sufficient to withstand inadvertent separation during bathing or washing by a user. By "water insoluble" is meant the substrate does not dissolve or readily break apart upon immersion in water. A wide variety of materials can be used for either substrate provided they fall within the constraints defined below. The following non-limiting characteristics are desirable: (i) sufficient capacity for releasably containing a cleansing composition, (ii) sufficient wet strength for use, (iii) sufficient abrasivity, (iv) sufficient loft and porosity, (v) sufficient thickness, and (vi) appropriate size to fit substantially within a user's hand.

Absorbent/Adsorbent Insoluble Substrates

Non-limiting examples of suitable absorbent/adsorbent insoluble substrates include sponge, woven or nonwoven fabrics and laminates of sponge and fabric and equivalent single and composite materials. Preferably such materials will posess a Compressibility Factor of at least 5% as defined above. Examples of suitable sponge materials include natural or synthetic materials commonly derived from wood fibers or foamed plastic polymers. Foamed plastic sponges include low-density polyether, PVA, polyurethane and polyester. Examples of suitable nonwoven substrates include either singly or in admixture of natural or synthetic fibers such as cellulose, wood pulp, rayon, polyester, polypropylene, polyethylene, polyamide, animal skin and the like suitably produced by wet-laid, dry-laid, spun bonded, hydroentangled, air-laid, and equivalent processes. By non-woven is meant that the layer is comprised of fibers which are not woven into a fabric but rather are formed into a sheet. The fibers can either be random (i.e., randomly aligned) or they can be carded (i.e. combed to be oriented in primarily one direction). Furthermore, the non-woven substrate can be composed of a combination of layers of random and carded fibers. Woven substrates consist of a planar structure produced by weaving or interlacing two or more sets of fibers or filaments as described above where the elements pass each other essentially at right angles and one set of elements are parallel to the fabric axis.

Scrubbing Substrate

The inventive cleansing includes at least one scrubbing substrate that is capable of producing a substantial quantity of lather when contacted with the inventive low active cleansing composition and rubbed between the hands during cleansing with water. A preferred scrubbing substrate is a polymeric mesh sponge comprising a plurality of plies of an extruded tubular netting mesh prepared from nylon or a strong flexible polymer, such as addition polymers of olefin monomers and polyamides of polycarboxylic acids.

Preferably the tubular netting has a maximum transverse expanded diameter of about 8 to 16 inches with the contracted minimum diameter on the order of about ½ inch. The tubular netting is preferably open at both ends so that it can be easily utilized in making the multi-ply netting for the preparation of the scrubbing section. The netting is prepared from fine filaments of polymeric material having a thickness preferably varying from about 10 to 18 mils. The netting is prepared from as many as 50 to 200 such filaments which appear to cross over each other at a 45.degree. angle and are bonded at junction points at intervals varying from about 3/16 to ½ inch, depending upon the type of netting or fabric desired. It is important that the bonding of the filaments at the indicated intervals be of such a nature as to securely attach the filaments together and provide a strong netting for the cleaning action. The bonding is preferably accomplished by the extruding technique, heat sealing the filaments together or by use of appropriate adhesives. Additional examples of suitable scrubbing material are disclosed in U.S. Pat. No. 4,462,135 issued on Jul. 31, 1984 and herein incorporated by reference.

Lathering Surfactant

The inventive personal care product contains a low active liquid cleansing composition with a maximum total amount of 8% by wt. of lathering surfactant(s) By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

A wide variety of lathering surfactants is useful herein and include those selected from anionic, nonionic, cationic, and amphoteric surfactants and mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3-M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$-$C_{16}$ olefin sulfonate, available as Bioterge AS 40®

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 1 or 2 moles average ethoxylation, commercially available as e.g. Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3-M+)CO_2R^2$ where $R^1$ is straight or branched alkyl from about $C_8$- to $C_{18}$, preferably $C_{12}$ to $C_{16}$, an $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 18 carbon atoms, with sodium lauryl lactylate sold as Pationic 138 C® available from the Patterson Chemical Company as the most preferred.

(13) Taurates having from 8 to 16 carbon atoms, with cocoyl methyl taurate being preferred.

(14) Fatty acid soaps consisting of soluble soaps. Soluble soap is defined as a soap or soap blend having a Krafft point less than or equal to about 40° C. The soluble soap(s) can be selected from the chain length of C6-C14 saturated fatty acid soap(s) and C16-C18 unsaturated and polyunsaturated fatty acid soap(s) or a combination of these fatty acid soaps. These soluble soaps can be derived from coco fatty acid, Babasu fatty acid, palm kernel fatty acid and any other source of unsaturated fatty acid including tallow and vegetable oils and their mixtures.

Nonionic lathering surfactants suitable for the present invention include $C_{10}$-$C_{20}$ fatty alcohol or acid hydrophobes condensed with from 2 to 100 moles of ethylene oxide or propylene oxide per mole of hydrophobe; $C_2$-$C_{10}$ alkyl phenols condensed with from 2 to 20 moles of alkylene oxides; mono- and di- fatty acid esters of ethylene glycol such as ethylene glycol distearate; fatty acid monoglycerides; sorbitan mono- and di- $C_8$-$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethylododecylamine oxide, oleyldi(2-hydroxyethyl)amine oxide, dimethyloctylamine oxide, dimethyldecylamine oxide, dimethyltetradecylamine oxide, di(20-hydroxyethyl)tetradecylamine oxide, 3-didodecyoxy-2-hydroxypropyldi(3-hydroxypropyl)amine oxide, and dimethylhexadecylamine oxide.

Suitable amphoteric or zwitterionic lathering surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 30 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, disodium cocoamphodiacetate, cocamidopropyl hydroxysultaine, and sodium cocoamphopropionate, which are particularly suitable as mild-type cleansers for skin and hair.

Thickeners

Suitable thickener(s) or structurant(s) may be optionally used in the inventive low active composition in a concentration effective to attain a desired viscosity level. Suitable structurant(s) or thickener(s) will maintain the inventive dilution profile where the viscosity decreases to 0.1 Pa·S or below after dilution of the low active composition with water using a dilution factor of 1.5 or 2.0 as measured at 35° C. and 10 s−1 shear rate at the total thickener/structurant concentration employed.

Hydrophilic Conditioning Agents

Skin hydrophilic conditioning agents also known as hydrophilic emollients may be advantageously used in the present invention as benefit agents. The emollient "composition" may be a single agent component or it may be a mixture of two or more compounds one or all of which may have a conditioning aspect. In addition, the conditioning agent itself may act as a carrier for other components one may wish to add to the personal care implement.

Hydrophilic emollients are preferably present in a concentration range of 0 to about 10% by weight of the cleansing composition contained in or added to the absorbent/adsorbent water insoluble substrate. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful examples of hydrophillic emollients (also known as humectants) include polyhydric alcohols, e.g. glycerine and propylene glycol, and the like; polyols such as the polyethylene glycols listed below and the like; saccharide(s) and/or polysaccharide(s) such as sucrose, sorbitol; and urea derivatives such as hydroxyethyl urea and the like may be advantageously used.

Other useful examples of hydrophillic emollients include any of the following or blends thereof: alcaligenes polysaccharides; algae extract; aloe barbadensis leaf extract; bacillus/rice bran extract/soybean extract ferment filtrate; black strap powder; diglycereth-7 malate; diglycerin; diglycol guanidine succinate; erythritol; fructose; glucose; glucoronolactone; glycereth-7 glycolate; glycerin; glyceryl dimaltodextrin; glycol; hesperetin laurate; 1,2,6-hexanetriol; honey; hydrogenated honey; hydrogenated starch hydrolysate; hydrolyzed wheat protein/PEG-20 acetate copolymer; hydroxypropyltrimonium hyaluronate; inositol; lactic acid; lacitol; maltitol; maltose; mannitol; mannose; methoxy PEG-7; methoxy PEG-10; methoxy PEG-16; methoxy PEG-25; methoxy PEG-40; methoxy PEG-100; PEG 4; PEG-6; PEG-7; PEG-8; PEG-9; PEG-10; PEG-12; PEG-14; PEG-16; PEG-18; PEG-20; PEG-32; PEG-40; PEG-45; PEG-55; PEG-60; PEG-75; PEG-90; PEG-75; PEG-90; PEG-100; PEG-135; PEG-150; PEG-180; PEG-200; PEG-220; PEG-240; PEG-800; PEG-15 butanediol; PEG-3-methyl ether; PEG-4 methyl ether; PEG-5 pentaerythrityl ether; polyglyceryl sorbitol; potassium dextrin octenylsuccinate; potassium PCA; PPG-6 sorbeth-245; PPG-6 sorbeth-500; propylene glycol; rosa canina seed extract; sodium acetylated hyaluronate; sodium dextrin octenylsuccinate; sodium glucuronate; sodium PCA; sorbeth-6; sorbeth-20; sorbeth-30; sorbeth-40; sorbitol; sorbityl silanediol; sucrose; TEA dextrin octenylsuccinate; trehalose; triglycereth-7 citrate; trioxaundecanedioic acid; tripropylene glycol; urea; urea-d-glucuronic acid; xylitol; xylose and the like.

Manufacturing methods

In a preferred embodiment, the cleansing products of the present invention are manufactured by separately or simultaneously adding onto or impregnating into absorbent/adsorbent water insoluble substrate a lathering surfactant and optionally a conditioning agent. By "separately" is meant that the components can be added sequentially, in any order without first being combined together. By "simultaneously" is meant that the components can be added at the same time, with or without first being combined together.

The components and any optional ingredients can be added onto or impregnated into the water insoluble absorbent/adsorbent substrate by any means known to those skilled in the art. For example, addition can be through spraying, printing, splashing, dipping, soaking, or coating, flood coating, spray coating or metered dosing prior to consumer use. The pre-saturated cleansing implement is then typically packaged in any of the moisture and vapor impermeable packages known in the art. In another preferred embodiment, the washing implement may be manufactured without the low active cleansing composition. A cleansing composition contained in a bottle or sachet may be provided separately or packaged together with the implement in a kit and the composition added to the implement by the consumer just prior to cleansing or bathing.

Method of Using the Cleansing Implements

For treatment of the user's skin or hair, the cleansing implement containing the low active cleansing composition is saturated with water, hand squeezed with a pressure of 3 to 12 psi to wet the scrubbing substrate with the cleansing composition, manipulated manually to generate a lather, which is applied to a surface (e.g., skin or hair surface) via topical application to release or deposit an effective amount of the aqueous liquid composition to perform the desired cleansing function. The amount of water-insoluble conditioning agent delivered from the implement and frequency of topical application can vary widely, depending upon the individual user's needs. With respect to personal application to the skin, such application can range from about once per day to about four times daily, preferably from about twice per day to about three times daily. The implements of the present invention can also be used prophylactically by administrating to healthy skin surfaces to guard from or prevent undesired skin conditions and/or infections using the dosing regimen described above.

Except in the operating and comparative examples, or where otherwise explicitly indicated, all numbers in this description indicating amounts of material ought to be understood as modified by the word "about".

The following non-limiting examples will more fully illustrate the embodiments of this invention. All parts, percentages and proportions referred to herein and in the appended claims are by weight unless otherwise illustrated.

EXAMPLE 1

Five implements: a) a mesh scrubber, b) a mesh scrubber attached to an open cell, cellulose sponge, c) a mesh scrubber attached to a woven cloth, d) a mesh scrubber attached to a non-woven cloth, and e) an open cell, cellulose sponge were variously tested for lather foam production with a low active liquid body wash composition (see Tables 1 to 3) with and without a structurant or thickener (acrylate polymer or starch) according to the procedure described below. The viscosity of the cleansing composition without the structurant was determined to be 0.001 Pas at 10 s−1 shear rate and 35° C. (i.e. water-like viscosity) while the composition with the structurant had a viscosity in the range of 1.7 to 5 Pa·s measured at the same shear rate and temperature (see viscosity measurement procedure described below). As a further comparison, implements (a) and (e) were also tested with a comparative high active body wash composition (see Table 4) using the same procedure. Lather foam volume results are listed in Table 5 and illustrated in FIG. 7.

TABLE 1

Formulation of low active cleansing composition with acrylate structurant "LA W/U20".

| Material | INCI Name | Supplier | Class | % Active |
|---|---|---|---|---|
| Hostapon SG ® | Na Glycinate | Clariant | Surfactant | 3.5 |
| Mackam HPL-28 ® | Amphoacetate | McIntyre | Surfactant | 2 |
| Ultrez 20 ® | Acrylates/C10-30 Alkyl Acrylate Crosspolymer | Lubrizol | Structurant Polymer | 1 |
| VERSENE 100XL ® | TETRASODIUM EDTA | Dow Chemical | Chelating agent | 0.05 |
| Kathon CG ® | Methylchloro-isothiazolinone | Rohm & Haas | Preservative | 0.0003 |
| Water |  |  |  | to 100 |
| NaOH (50%) approx. |  | BDH | pH adjustment |  |

Formulation protocol: Add water to kettle. Add Ultrez 20®. Keep bath at 60° C. while stirring. Add amphoacetate. Then add glycinate and other ingredients. Check pH. Add NaOH to adjust to pH~7

TABLE 2

Formulation of low active cleansing composition without added structurant "LA W/O U20 or Starch".

| Material | INCI Name | Supplier | Class | % Active |
|---|---|---|---|---|
| Hostapon SG ® | Na Glycinate | Clariant | Surfactant | 3.5 |
| Mackam HPL-28 ® | Amphoacetate | McIntyre | Surfactant | 2 |
| VERSENE 100XL ® | TETRASODIUM EDTA | Dow Chemical | Chelating agent | 0.05 |
| Kathon CG ® | Methylchloro-isothiazolinone | Rohm & Haas | Preservative | 0.0003 |
| Water |  |  |  | to 100 |
| NaOH (50%) approx |  | BDH | pH adjustment |  |

Formulation protocol: Add water to kettle. Keep bath at 60° C. while stirring. Add amphoacetate. Then add glycinate and other ingredients. Check pH. Add NaOH to get to pH~7

TABLE 3

Formulation of low active cleansing composition with starch structurant "LA W/Starch".

| Material | INCI Ingredient | Supplier | Class | % Activity | % Active level |
|---|---|---|---|---|---|
| Hostapon SG | Na Glycinate | Clariant | Surfactant | 25 | 3.5 |
| Mackam HPL-28 | Amphoacetate | McIntyre | Surfactant | 28 | 2 |
| Puregel B990/Food Starch-Modified | Starch | Grain Processing Corp. | Structurant | 100 | 7 |
| VERSENE 100XL | TETRASODIUM EDTA | Dow Chemical | Chelating agent | 39 | 0.05 |
| Kathon CG | Methylchloro isothiazolinone | Rohm & Haas | Preservative | 1.5 | 0.0003 |
| Water | | | | 100 | to 100 |
| Citric Acid(50%) approx | | VWR | pH adjustment | | |

Formulation protocol: Add water to the kettle and heat to 70° C. followed by Starch. Cook Starch at 70° C. for 15 min. Then add Glycinate and mix and then add Amphoacetate. Adjust the pH to ~7 by adding citric acid.

TABLE 4

Formulation of a comparative high active cleansing composition ("High Active").

| Material | INCI Ingredient | Supplier | Class | % Active |
|---|---|---|---|---|
| Aqua SF-1 ® | Carbopol | Lubrizol | Structurant Polymer | 1-3% |
| SLES | Sodium lauryl ether sulfate (1EO) | Stepan | Surfactant | 9-15% |
| CMEA | Cocamide monoethanolamine | Cognis | Surfactant | 1-3% |
| Betaine | Cocamidopropyl Betaine | Stepan | Surfactant | 0.5-3% |
| VERSENE 100XL ® | TETRASODIUM EDTA | Dow Chemical | Chelating agent | 0.05% |
| Glycerin | Glycerin | Cognis | Emollient | 0.1%-0.5% |
| Jaguar C13S ® | Guar Hydroxypropyl trimonium Chloride | Rhodia | Deposition aid | 0.1-0.5% |
| Citric Acid | Citric Acid | VWR | pH adjuster | 0.0500% |
| Kathon CG ® | Methylchloro isothiazolinone | Rohm & Haas | Preservative | 0.0003% |
| sodium chloride solution | salt | VWR | Viscosity adjuster | 1.0%-2.0% |
| DI Water | Water | | | to 100 |

Formulation protocol: Add Water to Kettle and begin heating to 65° C. and add CMEA and let it melt. Bring temperature down to room temperature (~20 to 25° C.) and add SLES. Then add Betaine followed by other ingredients. Make a blend of Jaguar & glycerin separately and add to the batch, followed by cold water. Add citric acid to adjust the pH to 7.

TABLE 5

Comparison of lather volume production for various implements with low and high active liquid cleansers of Tables 1-4:

| | LA W/U20 | | LA W/O U20 or Starch | | High Active | | LA W/STARCH | |
|---|---|---|---|---|---|---|---|---|
| Implement | $F_{avg} \pm F_{stdev}$ | Inv./Comp. | $F_{avg} \pm F_{stdev}$ | Inv./Comp. | $F_{avg} \pm F_{stdev}$ | Inv./Comp. | $F_{avg} \pm F_{stdev}$ | Inv./Comp. |
| a) Scrubber | 506 ± 85 | C | 794 ± 80 | C | 1358 ± 80 | C | 725 ± 54 | C |
| b) Scrubber + Sponge | 798 ± 50 | C | 1078 ± 90 | I | | | 1031 ± 106 | I |
| c) Scrubber + Non-woven | 672 ± 58 | C | 986 ± 89 | I | | | | |
| d) Scrubber + Woven | 572 ± 82 | C | 716 ± 29 | I | | | | |
| e) Sponge | 183 ± 29 | C | 367 ± 29 | C | 567 ± 58 | C | | |

Typical high active cleansing compositions (containing more than 10 or 12% by wt. of total surfactants) such as conventional commercially available body washes de-structure rapidly upon dilution with water because of the phase change that occurs in those systems. Although not wishing to be bound by the following theory it is believed that the surfactants transform from a worm-like micelle (WLM) structure (which provides the bulk of structuring) to regular micelles (which provide no structuring) on dilution. It is believed that the low concentration of surfactants in low active systems that is a component of the inventive product preclude them from forming WLM structure. If a higher viscosity is desired, a suitable thickener or structurant may be selected to provide the required structuring while maintaining the inventive dilution profile as discussed above.

Dilution profiles with respect to the change in viscosity with dilution were measured for the low active and high active compositions shown in Tables 1-4. The data is summarized in Table 6 and illustrated in FIG. 8. The dilution profiles of a conventional high active body wash is shown using triangles and that of the low active system with U20 polymer is shown using squares. One can see that the high active sample de-structures more rapidly than the LA w/U20 polymer. This also shows that the dilution profile for LA w/U20 is outside the inventive criteria (see FIGS. 7 and 8) and not conducive to lathering as shown in Table 5.

TABLE 6

Variation of viscosity with dilution for low and high
active compositions (1):
Viscosity at 10 s$^{-1}$ (Pa · s)

| Dilution | High Active | LA w/U20 | LA w/o U20 | LA w/Starch |
|---|---|---|---|---|
| 0 | 8.344 | 4.910 | 0.001 | 1.700 |
| 1.33 | 0.673 | 2.251 | | |
| 2 | 0.027 | 1.000 | | 0.025 |
| 3 | 0.003 | 0.256 | | 0.005 |
| 10 | 0.001 | 0.010 | | 0.002 |

(1) See Tables 1-4

Figure 7:
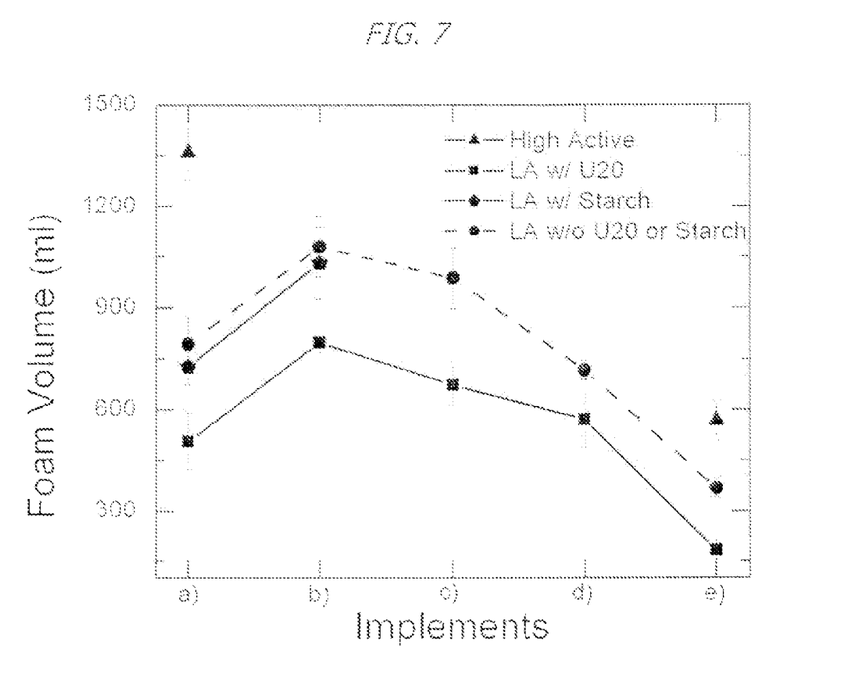
FIG. 7 is a line graph showing a comparison of lather foam volume generation using inventive and comparative implements listed in Table 5.
Figure 8:
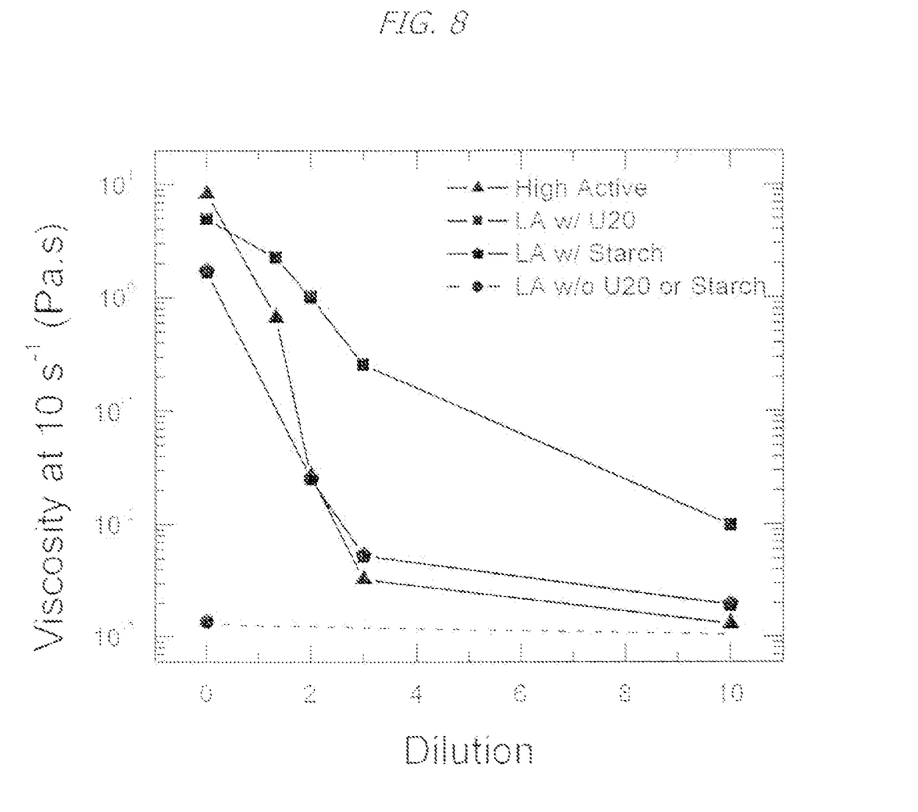
FIG. 8 is a line graph showing the relationship between viscosity and dilution factor with water for inventive and comparative cleansing compositions listed in Tables 1-4.

It was further surprisingly found that for all the implements tested, more lather was generated for the LA w/o structurant composition than the formulation with the LA w/structurant composition (See FIG. 7 and Tables 1 to 3). Comparing implements (a) and (b), it was also observed that inventive product implement (b) provided a boost to the lather volume for the LA formulations tested.

Furthermore, it was unexpectedly found that by using an inventive product implement (b) and formulating without the structurant (or within the required dilution profile), a low active system generates almost twice as much lather foam e.g. a lather volume of 1078 ml compared to a lather volume of 506 ml for implement (a) alone. The other implements included in the inventive product show very good to excellent lather volume as well with the low active compositions in contrast to the lower foam volume for comparative implement (e).

Implement Description:
Sponge: dimensions 7×5.5×4.5 cm or 173.25 cm$^3$ Volume; open cell made of cellulose material (Consumers Interstate Corporation; part no. SS0109-11; Norwich, Conn.).
Woven: dimensions 18×14 cm or 252 cm$^2$ Area; Mainstays True Colors®, 100% cotton, available from Wal-Mart.
Non-Woven: dimensions 24×19 cm$^2$ or 456 cm$^2$ Area; dot coated 50% rayon and 50% polyester, 55-65 gsm (Ahlstrom Corporation, Helsinki, Finland).
Both the woven and non-woven are folded to approximately 7.5×7.5 cm size before being affixed to the scrubber.
Scrubber material: dimensions approximately 9 cm in diameter, obtained from Bensussen Deutsch & Associates, Inc., Woodinville, Wash. as part no. 243206, 18 g LDPE (Low-density polyethylene).

Experimental test methods:
A. Lather Foam Measurement:
1. Thoroughly wet implement in lukewarm water (T=37° C.).
2. Squeeze water out by hand.
3. Add 5 ml of cleansing composition directly onto the scrubber.
4. Generate lather by kneading implement between two hands 15×.
5. Place a 1000 ml capacity beaker underneath the implement to collect any lather that falls.
6. Place lathered hands inside an inverted funnel having a connected flexible tube with a free open end.
7. Place outlet tube free end inside the beaker.
8. Lower the inverted funnel and hands together in water.
9. Allow substantially all lather to be collected (usually 1-3 minutes).
10. Measure the volume of the lather in beaker.
11. Measure the volume of the lather in flexible tube.
12. The total lather foam volume is the sum of the two measurements.

B. Viscosity measurement:
1. AR-G2 rheometer (available from TA Instruments, New Castle, Del.) is used to measure the viscosity of the samples.
2. Double wall couette geometry is used.
3. Steady state flow rate measurement is done over a shear rate range of 0.01 to 1000/s.

We claim:

1. A cleansing product, comprising:
a. an implement including a first layer attached to a second layer, wherein the first layer is composed of a water insoluble scrubbing substrate and the second layer is composed of a water insoluble absorbent/adsorbent substrate;
b. a low active liquid cleansing composition containing about 0.1 to 8% by wt, of total lathering surfactant(s);
c. wherein the liquid cleansing composition is contained in the second layer;
d. wherein the second layer can retain at least 5 grams of the liquid cleansing composition and wherein the second layer has a Compressibility Factor of at least 5%; and
e. wherein the liquid cleansing composition contains water soluble or dispersible thickener(s) in a concentration effective to attain a desired viscosity level and to maintain a dilution profile whereby the viscosity is lowered to 0.1 Pa.s or less measured at a water dilution factor of 1.5 or 2.0 and a shear rate of 10 s$^{-1}$ at 35° C.

2. The cleansing product of claim 1 wherein the scrubbing substrate is composed of polymeric mesh sponge having a plurality of plies of an extruded tubular netting mesh and the second layer is composed of material selected from sponge material, fibrous material or a combination thereof.

3. The cleansing product of claim 1 wherein the length of the implement along its major axis is less than 15 cm.

4. The cleansing product of claim 1 wherein the water soluble or dispersible thickener(s) have a maximum concentration of about 10% by wt.

5. The cleansing product of claim 1 further comprising hydrophilic conditioning agent(s) in a total concentration range of 0 to about 10% by wt.

6. The cleansing product of claim 1 wherein lather foam volume as measured by a standard Lather Foam Measurement test is greater than 700 mls.

7. The cleansing product of claim 1 wherein the first layer is arranged substantially around the second layer.

8. The cleansing product of claim 1 wherein the first layer and second layer are positioned in a substantially side by side arrangement.

9. The cleansing product of claim 1 wherein the second layer has the capacity to contain about 5 to 40 gms of the liquid cleansing composition.

10. The cleansing product of claim 1 wherein the liquid cleansing composition includes lathering surfactants selected from soap, synthetic anionic surfactant(s), cationic surfactant(s), amphoteric surfactant(s), nonionic surfactants or blends thereof.

11. A cleansing product kit, comprising;
   a. A substantially dry implement including a first layer attached to a second layer, wherein the first layer is composed of a scrubbing substrate and the second layer is composed of an absorbent/adsorbent substrate;
   b. a liquid cleansing composition supplied in a container in combination with the implement containing about 0.1 to 8% by wt. of total lathering surfactant(s);
   c. wherein the second layer can contain at least 5 grams for the liquid cleansing composition and has a Compressibility Factor of at, least 5%;
   d. optionally instructions for use of he cleansing product kit; and
   e. wherein the liquid cleansing composition contains water soluble or dispersible thickerner(s) in a concentration effective to attain a desired vicosity level and to maintain a dilution profile whereby the viscosity is lowered to 0.1 Pa.s or less measured at a water dilution factor of 1.5 or 2.0 and a shear rate of 10 $s^{-1}$ at 35° C.

12. A method of cleansing skin or hair comprising the steps of:
   a. providing a cleansing implement including a first layer attached to a second layer, wherein the first layer is composed of a scrubbing substrate and the second layer is composed of an absorbent/adsorbent substrate,
   b. wherein the second layer is supplied with at least 5 grams of a cleansing composition containing about 0.1 to 8% by wt. of total lathering surfactant(s) prior to cleansing the skin or hair;
   c. adding water to the implement while manually compressing and releasing the implement to transfer a sufficient quantity of cleansing composition to the scrubbing substrate to generate lather; and
   d. wherein the liquid cleansing composition contains water soluble or dispersible thickener(s) in a concentration effective to attain a desired viscosity level and to maintain a dilution profile whereby the viscosity is lowered to 0.1 Pa.s or less measured at a water dilution factor of 1.5 or 2.0 and a shear rate of 10 $s^{-1}$ at 35° C.

\* \* \* \* \*